(12) United States Patent
Maubru et al.

(10) Patent No.: US 7,811,552 B2
(45) Date of Patent: Oct. 12, 2010

(54) COSMETIC COMPOSITION COMPRISING A MIXTURE OF SURFACTANTS, A MIXTURE OF CATIONIC POLYMERS AND A SILICONE

(75) Inventors: Mireille Maubru, Chatou (FR); Bruno Liebard, Chatillon (FR)

(73) Assignee: L'Oreal S.A., Paris (FR)

( * ) Notice: Subject to any disclaimer, the term of this patent is extended or adjusted under 35 U.S.C. 154(b) by 1249 days.

(21) Appl. No.: 10/900,086

(22) Filed: Jul. 28, 2004

(65) Prior Publication Data

US 2005/0100523 A1    May 12, 2005

Related U.S. Application Data

(60) Provisional application No. 60/503,475, filed on Sep. 17, 2003.

(30) Foreign Application Priority Data

Jul. 28, 2003    (FR) .................... 03 09240

(51) Int. Cl.
*A61Q 5/00*    (2006.01)
*A61Q 5/04*    (2006.01)
(52) U.S. Cl. .................... 424/70.12; 424/70.2; 424/401
(58) Field of Classification Search ........................ None
See application file for complete search history.

(56) References Cited

U.S. PATENT DOCUMENTS

| | | | |
|---|---|---|---|
| 2,528,378 A | 10/1950 | Mannheimer et al. |
| 2,781,354 A | 2/1957 | Mannheimer et al. |
| 3,472,840 A | 10/1969 | Stone et al. |
| 3,912,808 A | 10/1975 | Sokol |
| 3,986,825 A | 10/1976 | Sokol |
| 4,027,008 A | 5/1977 | Sokol |
| 4,031,307 A | 6/1977 | DeMartino et al. |
| 4,131,576 A | 12/1978 | Iovine et al. |
| 4,693,935 A | 9/1987 | Mazurek |
| 4,728,571 A | 3/1988 | Clemens et al. |
| 4,972,037 A | 11/1990 | Garbe et al. |
| 5,726,137 A | 3/1998 | Patel et al. |
| 6,007,802 A | 12/1999 | Coffindaffer et al. |
| 6,297,203 B1 | 10/2001 | Guskey et al. |
| 6,514,488 B1 | 2/2003 | Cauwet-Martin et al. |
| 6,706,258 B1 | 3/2004 | Gallagher et al. |
| 2001/0009909 A1 | 7/2001 | Maubru et al. |

FOREIGN PATENT DOCUMENTS

| | | |
|---|---|---|
| EP | 0 400 976 A1 | 12/1990 |
| EP | 0 412 704 A2 | 2/1991 |
| EP | 0 412 707 A1 | 2/1991 |
| EP | 0 582 152 A2 | 2/1994 |
| FR | 1 492 597 | 8/1967 |
| FR | 2 080 759 | 11/1971 |
| FR | 2 190 406 | 2/1974 |
| GB | 2 255 101 | 10/1992 |
| JP | 6-312915 | 8/1994 |
| JP | 2001-302466 | 10/2001 |
| WO | WO 93/23446 | 11/1993 |
| WO | WO 94/06403 | 3/1994 |
| WO | WO 95/00578 | 1/1995 |
| WO | WO 97/26860 | 7/1997 |
| WO | WO 98/50007 | 11/1998 |
| WO | WO 99/09947 | 3/1999 |
| WO | WO 93/23009 | 11/2003 |

OTHER PUBLICATIONS

English language Patent Abstract of Japan of JP-6-312915, Aug. 11, 1994.
English language Patent Abstract of Japan of JP-2001-302466, Oct. 31, 2001.

*Primary Examiner*—Jyothsna A Venkat
(74) *Attorney, Agent, or Firm*—Finnegan, Henderson, Farabow, Garrett & Dunner, L.L.P.

(57) ABSTRACT

A cosmetic composition for treating keratin fibers, such as the hair, comprising:
  at least one anionic surfactant;
  at least one second surfactant chosen from amphoteric and zwitterionic surfactants;
  at least one first cationic polymer chosen from cationic polysaccharides; and
  at least one second cationic polymer chosen from dialkyldiallylammonium homopolymers and copolymers; and
  at least one non-amino non-volatile silicone, and treatment processes using the composition.

22 Claims, No Drawings

COSMETIC COMPOSITION COMPRISING A MIXTURE OF SURFACTANTS, A MIXTURE OF CATIONIC POLYMERS AND A SILICONE

This application claims benefit of U.S. Provisional Application No. 60/503,475, filed Sep. 17, 2003.

Disclosed herein is a cosmetic composition for treating keratin fibers, such as hair, comprising a mixture of surfactants, a mixture of cationic polymers and at least one silicone, and cosmetic processes for treating keratin fibers using the composition.

Hair may be damaged and embrittled by the action of external atmospheric agents, such as light and bad weather, and mechanical or chemical treatments, such as brushing, combing, bleaching, permanent-waving and/or dyeing. As a result, hair may often be difficult to disentangle or to style. Moreover, even a thick head of hair may not easily maintain a good looking style due to the fact that the hair may lack vigor and liveliness.

It is known practice to protect hair against the effects of light by applying water-soluble or water-insoluble, polymeric or non-polymeric UV-screening agents, nanoparticles, antioxidants, metal-complexing agents, chelating agents, or free-radical scavengers. Further, embrittled hair may also be mechanically strengthened by applying thereto certain cationic polymers, alone or as a mixture with specific electrolytes.

In order to better disentangle the hair and to prevent the hair from having a certain level of coarseness, monomeric or polymeric, water-soluble or water-insoluble conditioners may also be applied thereto.

It is also known practice to add these various conditioners as a mixture with hair dye compositions, shampoos or other cosmetic compositions, in order to give the hair at least one of the following cosmetic properties-disentangling, feel, smoothness, sheen, and volume.

For example, Patent Application Publication No. WO 97/26860 relates to a conditioning shampoo composition that may disentangle wet or dry hair more easily, and may not irritate the eyes or sensitive skin. This composition comprises a mixture of surfactants and a mixture of conditioners.

However, compositions comprising conditioners as a mixture may present stability problems. There is a continued need for cosmetic compositions that have great stability and improved conditioning effects.

Patent Application Publication No. WO 94/06403 proposes to solve this stability problem. This application relates to a stable hair-conditioning shampoo composition comprising agents with conditioning properties and agents usually used in shampoos. This stable composition comprises an anionic surfactant, a cationic vinyl polymer, a hair conditioner, a dispersant for stabilizing the composition, and water.

Japanese Patent Application No. 46-312915 relates to a hair treatment composition comprising quaternized guar gum and a cationic polymer. This type of composition may make it possible to obtain uniform conditioning effects on the hair, for example, wet hair that is smoother during washing and rinsing, a non-greasy appearance, or greater stability of the composition over time.

However, these compositions may not be sufficiently stable and may have at least one drawback not only with regard to the working qualities of the composition, for example, insufficient production of lather, but also with regard to the cosmetic qualities of the hair, for example, giving the hair a coarse feel.

The present inventors have discovered that the combination of a mixture of surfactants, a mixture of cationic polymers and a silicone may make it possible to obtain cosmetic compositions that may be more stable than the compositions previously described, and may have at least one better working or cosmetic quality. For example, the composition disclosed herein may make it possible to obtain an abundant lather upon application and give wet hair great softness. Further, these novel compositions may give curly hair good curl definition and smoothness.

Further disclosed herein is a cosmetic process for treating a keratin material using the compositions described above.

Other subjects, characteristics, aspects and advantages of the embodiments disclosed herein will emerge even more clearly on reading the description and the various examples that follow.

Disclosed herein is a cosmetic composition for cosmetically treating keratin fibers, such as hair, comprising:
- at least one anionic surfactant;
- at least one second surfactant chosen from amphoteric and zwitterionic surfactants;
- at least one first cationic polymer chosen from cationic polysaccharides;
- at least one second cationic polymer chosen from dialkyldiallylammonium homopolymers and copolymers; and
- at least one non-amino non-volatile silicone, wherein the total amount of surfactants in the composition ranges from 4.5% to 20% by weight, relative to the total weight of the composition.

Anionic Surfactant

In one embodiment, the at least one anionic surfactant may be chosen, for example, from salts, such as alkali metal salts, for example, sodium salts, ammonium salts, amine salts, amino alcohol salts, and magnesium salts, of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; $(C_6-C_{24})$alkyl sulfosuccinates, $(C_6-C_{24})$alkyl ether sulfosuccinates, $(C_6-C_{24})$alkylamide sulfosuccinates; $(C_6-C_{24})$alkyl sulfoacetates; $(C_6-C_{24})$acyl sarcosinates; and $(C_6-C_{24})$acyl glutamates.

It is also possible to use $(C_6-C_{24})$alkylpolyglycoside carboxylic esters, such as alkylglucoside citrates, alkylpolyglycoside tartrates and alkylpolyglycoside sulfosuccinates, alkylsulfosuccinamates; acyl isethionates and N-acyl taurates, wherein the alkyl or acyl radical of all of these different compounds may comprise, for example, from 12 to 20 carbon atoms and the aryl radical may be chosen from phenyl and benzyl groups. Examples of the at least one anionic surfactant which can also be used include fatty acid salts, such as oleic, ricinoleic, palmitic and stearic acid salts, coconut oil acid and hydrogenated coconut oil acid; acyl lactylates, wherein the acyl radical comprises 8 to 20 carbon atoms.

It is also possible to use alkyl D-galactoside uronic acids and salts thereof, polyoxyalkylenated $(C_6-C_{24})$alkyl ether carboxylic acids, polyoxyalkylenated $(C_6-C_{24})$alkylaryl ether carboxylic acids, polyoxyalkylenated $(C_6-C_{24})$alkylamido ether carboxylic acids and salts thereof, for example, those comprising from 2 to 50 alkylene oxide groups, for example, ethylene oxide groups, and mixtures thereof.

In one embodiment, alkyl sulfates and alkyl ether sulfates may be used.

The at least one anionic surfactant may be present in an amount ranging from 0.01% to 40%, for example, from 0.5% to 30%, further, for example, from 4% to 25%, and, even further, for example, from 4% to 19% by weight, relative to the total weight of the composition.

Second Surfactant

The at least one second surfactant chosen from amphoteric and zwitterionic surfactants may, for example, be chosen from amines and quaternary ammoniums bearing at least one chain chosen from linear and branched chains comprising 8 to 18 carbon atoms and comprising at least one water-solubilizing anionic group, for example, chosen from carboxylate, sulfonate, sulfate, phosphate, and phosphonate groups.

Examples of the at least one second surfactant include $(C_8-C_{20})$alkylbetaines, sulfobetaines, $(C_8-C_{20})$alkylamido$(C_1-C_6)$alkylbetaines and $(C_8-C_{20})$alkylamido$(C_1-C_6)$alkylsulfobetaines. In one embodiment, cocoylbetaine and cocoamidopropylbetaine may be used in the composition disclosed herein.

Examples of amphoteric amines include the products sold under the name Miranol, as described in U.S. Pat. Nos. 2,528,378 and 2,781,354 and classified in the CTFA dictionary, 3rd edition, 1982, under the names Amphocarboxyglycinates and Amphocarboxypropionates, with the respective structures:

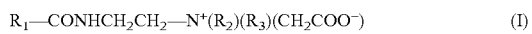

$$R_1\text{—CONHCH}_2\text{CH}_2\text{—N}^+(R_2)(R_3)(\text{CH}_2\text{COO}^-) \qquad (I)$$

wherein:
- $R_1$ is chosen from $C_5-C_{20}$ linear and branched alkyl radicals derived from an acid $R_1$—COOH present in hydrolyzed coconut oil and heptyl, nonyl, and undecyl radicals;
- $R_2$ is a beta-hydroxyethyl group; and
- $R_3$ is chosen from a carboxymethyl group and

$$R_4\text{—CONHCH}_2\text{CH}_2\text{—N(B)(D)} \qquad (II)$$

wherein:
- B is chosen from groups —$CH_2CH_2OX$;
- D is chosen from groups —$(CH_2)_z$—Y, wherein z=1 or 2;
- X is chosen from a —$CH_2CH_2$—COOH group and a hydrogen atom;
- Y is chosen from —COOH and a —$CH_2$—CHOH—$SO_3H$ radical; and
- $R_4$ is chosen from saturated and unsaturated, linear and branched $C_5-C_{20}$ alkyl radicals derived from an acid $R_4$—COOH present, for example, in coconut oil and in hydrolyzed linseed oil; alkyl radicals, such as $C_7$, $C_9$, $C_{11}$, and $C_{13}$ alkyl radicals; a $C_{17}$ alkyl radical and an iso form thereof; and an unsaturated $C_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid and Cocoamphodipropionic acid.

A further example of the amphoteric amines include cocoamphodiacetate sold under the trade name Miranol® C2M Concentrate by the company Rhodia Chimie.

In one embodiment, the at least one second surfactant chosen from zwitterionic and amphoteric surfactants are chosen from alkylbetaines, amidoalkylbetaines and alkylamphodiacetate.

The at least one second surfactant chosen from amphoteric and zwitterionic surfactants may be present in an amount ranging, for example, from 0.01% to 40% by weight, further, for example, from 0.5% to 30% by weight, and, further, for example, from 1% to 10% by weight, relative to the total weight of the composition.

The total amount of surfactants present in the composition disclosed herein ranges from 4.5% to 20% by weight, relative to the total weight of the composition.

In one embodiment, the at least one anionic surfactant and the at least one second surfactant chosen from amphoteric surfactants and zwitterionic surfactants are present such that the weight ratio of the at least one anionic surfactant to the at least one second surfactant is greater, for example, than 1.5:1, further, for example, ranges from 2:1 to 20:1, and, even further, for example, ranges from 2:1 to 10:1.

First Cationic Polymer

As used herein, the expression "cationic polymer" means any polymer comprising cationic groups and/or groups that can be ionized into cationic groups.

The cationic polymers that may be used have a number-average molecular mass ranging from 500 to $5 \times 10^6$ and, further, for example, $10^3$ to $3 \times 10^6$.

The composition disclosed herein comprises at least one first cationic polymer chosen from cationic polysaccharides, for example, cationic celluloses and cationic guar gums.

The at least one first cationic polymer may be chosen from cellulose ether derivatives comprising at least one quaternary ammonium group, described in French Patent No. 1,492,597, and, for example, polymers sold under the names "JR" (JR 400, JR 125 and JR 30M) and "LR" (LR 400 or LR 30M) by the company Amerchol. These polymers are also defined in the CTFA dictionary as quaternary ammoniums of hydroxyethylcellulose that have reacted with an epoxide substituted with a trimethylammonium group.

The at least one first cationic polymer may also be chosen from cationic cellulose derivatives, such as cellulose derivatives grafted with at least one water-soluble quaternary ammonium monomer, and described, for example, in U.S. Pat. No. 4,131,576, such as hydroxyalkylcelluloses, such as hydroxymethyl-, hydroxyethyl- and hydroxypropyl-celluloses grafted, for example, with at least one salt chosen from methacryloylethyl-trimethylammonium, methacrylamidopropyltrimethylammonium, and dimethyldiallyl-ammonium salts.

The commercial products corresponding to this definition are, for example, the products sold under the names "Celquat L 200" and "Celquat H 100" by the company National Starch.

The cationic guar gums are described, for example, in U.S. Pat. Nos. 3,589,578 and 4,031,307, such as guar gums comprising at least one cationic trialkylammonium group. Guar gums modified with at least one salt (for example, a chloride) of 2,3-epoxypropyltrimethylammonium, glycidyltrimethylammonium, 3-chloro-2-hydroxypropyltrimethylammonium may be used, for example.

Such products are sold, for example, under the trade names Jaguar C13 S, Jaguar C 15, Jaguar C 17, and Jaguar C162 by the company Rhodia Chimie.

In one embodiment, the cationic polysaccharides disclosed herein may be chosen from cationic guar gum derivatives.

In the composition disclosed herein, the at least one first cationic polymer may be present in an amount ranging from 0.01% to 10% by weight, further, for example, from 0.03% to 5% by weight, further, for example, from 0.05% to 2% by weight, and even further, for example, from 0.07% to 1% by weight, relative to the total weight of the composition.

Second Cationic Polymer

The composition disclosed herein further comprises at least one second cationic polymer chosen from dialkyldiallylammonium homopolymers and copolymers.

The polymers of alkyldiallylamine or of dialkyldiallylammonium, such as the homopolymers and copolymers comprising, as a main constituent of the chain, at least one unit chosen from units corresponding to formula (III) and (IV):

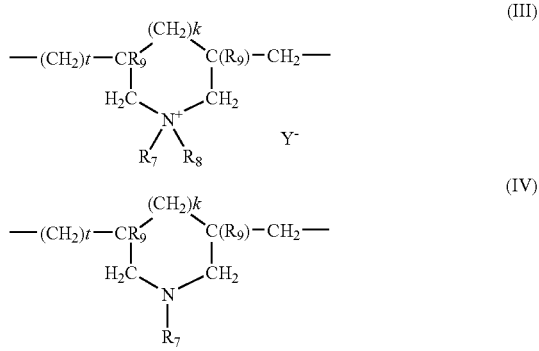

wherein: k and t are equal to 0 or 1, the sum k+t being equal to 1; $R_9$, which may be identical or different, may be chosen from a hydrogen atom and a methyl radical; $R_7$ and $R_8$, which may be identical or different, are each chosen from alkyl groups comprising from 1 to 6 carbon atoms, hydroxyalkyl groups, wherein the alkyl groups, for example, comprise from 1 to 5 carbon atoms, lower ($C_1$-$C_4$) amidoalkyl groups, and $R_7$ and $R_8$ can form, together with the nitrogen atom to which they are attached, at least one heterocyclic group, for example, chosen from piperidyl and morpholinyl groups; $R_7$ and $R_8$, which may be identical or different, are each chosen from alkyl groups comprising from 1 to 4 carbon atoms; $Y^-$ is an anion, for example, chosen from bromide, chloride, acetate, borate, citrate, tartrate, bisulfite, sulfate, and phosphate ions. These polymers are described, for example, in French Patent Nos. 2,080,759 and in its Additional Certificate No. 2,190,406.

Examples of the at least one second cationic polymer defined above include, for example, the dimethyldiallylammonium chloride homopolymer sold under the name Merquat® 100 by the company Nalco (and homologues thereof having a low weight-average molecular mass) and copolymers of diallyldimethylammonium chloride and of acrylamide, sold under the name "Merquats" and "Merquat 550".

For example, the at least second cationic polymer may be chosen from dialkyldimethylammonium chloride homopolymers and copolymers, and, further, for example, copolymers of diallylammonium and acrylamide.

In the composition disclosed herein, the at least one second cationic polymer may be present in an amount ranging from 0.01% to 10% by weight, further, for example, from 0.03% to 5% by weight, further, for example, from 0.05% to 2% by weight, and even further, for example, from 0.07% to 1% by weight, relative to the total weight of the composition.

Non-Amino, Non-Volatile Silicone

As used herein, in accordance with what is generally accepted, the term "nonvolatile silicone" or "polysiloxane" is understood to mean any organosilicone polymer or oligomer having a linear, branched or crosslinked structure of variable molecular weight, obtained by polymerization and/or polycondensation of suitably functionalized silanes, and comprising a repetition of main units wherein the silicon atoms are linked together by oxygen atoms (siloxane bonding =Si—O—Si=), wherein the optionally substituted hydrocarbon radicals are linked directly via a carbon atom to the silicon atoms. The hydrocarbon radicals may be chosen from alkyl radicals, for example, $C_1$-$C_{10}$ alkyl radicals, such as methyl;

fluoroalkyl radicals; aryl radicals, for example, a phenyl radical; alkenyl radicals and, for example, a vinyl radical; other types of radicals that can be linked, either directly or via a hydrocarbon radical, to the siloxane chain may, for example, be chosen from hydrogen; halogens, such as chlorine, bromine and fluorine atoms; thiols; alkoxy radicals; polyoxyalkylene, such as polyether radicals and, for example, polyoxyethylene and polyoxypropylene; hydroxyl and hydroxyalkyl radicals; amide groups; acyloxy radicals and acyloxyalkyl radicals; and anionic groups, such as carboxylates, thioglycolates, sulfosuccinates, thiosulfates, phosphates, and sulfates, needless to say this list not being limiting in any way (so-called "organomodified" silicones).

As used herein, the term "non-volatile silicone" means silicones wherein the number of silicon atoms is greater than 7.

As used herein, the term "non-amino silicone" means any silicone not comprising a primary, secondary or tertiary amine functional group or a quaternary ammonium group.

Examples of silicones that may be used in the compositions disclosed herein include polyorganosiloxanes that may be in the form of oils, waxes, resins or gums.

The organopolysiloxanes are defined in greater detail in Walter Noll's "Chemistry and Technology of Silicones" (1968) Academic Press.

Silicones, for example, polyalkylsiloxanes, polyarylsiloxanes, polyalkylarylsiloxanes, silicone gums, silicone resins, and polyorganosiloxanes modified with at least one organofunctional group, and mixtures thereof, may be used.

These silicones may, for example, be chosen from polyalkylsiloxanes, such as polydimethylsiloxanes comprising trimethylsilyl end groups, having a viscosity of $5 \times 10^{-6}$ at 2.5 $m^2$/s and, for example, $1 \times 10^{-5}$ at 1 $m^2$/s at 25° C.

Examples of these polyalkylsiloxanes include the following commercial products:

the Silbione® oils of the series 47 and 70 047 and the Mirasil DM oils sold by Rhodia Chimie, for example, the oil 70 047 V 500 000 and the oil Mirasil DM 300 000;

the oils of the Mirasil® DM series sold by the company Rhodia Chimie;

the oils of the 200 series from the company Dow Corning; and the Viscasil® oils from General Electric and certain oils of the SF series (SF 96, SF 18) from General Electric.

Mention may also be made of polydimethylsiloxanes comprising dimethylsilanol end groups (Dimethiconol according to the CTFA name) such as, the oils of the 48 series from the company Rhodia Chimie.

In this category of polyalkylsiloxanes, mention may also be made of the products sold under the names "Abil® Wax 9800 and 9801" by the company Goldschmidt, which are poly($C_1$-$C_{20}$)alkylsiloxanes.

The polyalkylarylsiloxanes may be chosen from linear and branched polydimethylmethylphenylsiloxanes and polydimethyldiphenylsiloxanes having a viscosity ranging from $1 \times 10^{-5}$ to $5 \times 10^{-2}$ $m^2$/s at 25° C.

Examples of polyalkylarylsiloxanes include the products sold under the following names:

the Silbione® oils of the 70 641 series from Rhodia Chimie;

the oils of the Rhodorsil 70 633 and 763 series from Rhodia Chimie;

the oil Dow Corning 556® Cosmetic Grade Fluid from Dow Corning;

the silicones of the PK series from Bayer, such as the product PK20;

the silicones of the PN and PH series from Bayer, such as the products PN1000 and PH1000; and certain oils of the SF series from General Electric, such as SF 1023, SF 1154, SF 1250 and SF 1265.

The silicone gums that can be used in the composition disclosed herein may be chosen from polydiorganosiloxanes having high weight-average molecular weights ranging from 200,000 to 3,000,000, used alone or as a mixture in at least one solvent. The at least one solvent can be chosen from volatile silicones, polydimethylsiloxane (PDMS) oils, polyphenylmethylsiloxane (PPMS) oils, isoparaffins, polyisobutylenes, methylene chloride, pentane, dodecane, and tridecanes.

Mention may be made, for example, of the following products:

polydimethylsiloxane,
polydimethylsiloxane/methylvinylsiloxane gums,
polydimethylsiloxane/diphenylmethylsiloxane,
polydimethylsiloxane/phenylmethylsiloxane, and
polydimethylsiloxane/diphenylsiloxane/methyl-vinylsiloxane.

Products that can be used in the composition disclosed herein may be chosen from mixtures, such as:

mixtures formed from a polydimethylsiloxane hydroxylated at the chain end (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a molecular weight of 500,000, dissolved in the oil SF 1202 Silicone Fluid corresponding to decamethylcyclopentasiloxane;

mixtures of two PDMSs of different viscosities, and, for example, a PDMS gum and a PDMS oil, such as the product SF 1236 from the company General Electric. The product SF 1236 is a mixture of an SE 30 gum defined above, having a viscosity of 20 m²/s, and an SF 96 oil, with a viscosity of 5×10⁻⁶ m²/s. This product, for example, comprises 15% SE 30 gum and 85% SF 96 oil.

The organopolysiloxane resins that can be used in the composition disclosed herein include crosslinked siloxane systems comprising the following units:

$R_2SiO_{2/2}$, $R_3SiO_{1/2}$, $RSiO_{3/2}$ and $SiO_{4/2}$, wherein R is chosen from hydrocarbon-based groups comprising 1 to 16 carbon atoms and a phenyl group. Among these products, mention may be made, for example, of the ones wherein R is chosen from $C_1$-$C_4$ lower alkyl radicals, for example, methyl, and a phenyl radical.

Among these resins, mention may be made of the product sold under the name "Dow Corning 593" and the sold under the names "Silicone Fluid SS 4230 and SS 4267" by the company General Electric, which are silicones of dimethyl/trimethyl siloxane structure.

Mention may also be made of the trimethyl siloxysilicate type resins sold, for example, under the names X22-4914, X21-5034 and X21-5037 by the company Shin-Etsu.

The organomodified silicones that can be used in the composition disclosed herein may be chosen from silicones as defined above and comprising in their structure at least one organofunctional group attached via a hydrocarbon-based radical.

Among the organomodified silicones, mention may be made of polyorganosiloxanes comprising:

thiol groups, such as the products sold under the names "GP 72 A" and "GP 71" from Genesee;

alkoxylated groups, such as the product sold under the name "Silicone Copolymer F-755" by SWS Silicones and Abil Wax 2428, 2434 and 2440 by the company Goldschmidt;

carboxylic anionic groups, such as the products described in European Patent Application No. EP 186 507 from the company Chisso Corporation, and alkylcarboxylic groups, such as those present in the product X-22-3701 E from the company Shin-Etsu; 2-hydroxyalkyl sulfonate; 2-hydroxyalkyl thiosulfate, such as the products sold by the company Goldschmidt under the names "Abil S201" and "Abil S255".

In one embodiment, the organomodified silicones do not have polyalkyleneoxy groups.

In one embodiment, it is also possible to use silicones comprising a polysiloxane portion and a portion comprising a nonsilicone organic chain, one of the two portions constituting the main chain of the polymer, wherein the other portion is grafted onto the main chain. These polymers are described, for example, in Patent Application Nos. EP-A412,704, EP-A412,707, EP-A-640,105, WO 95/00578, EP-A-582,152 and WO 93/23009 and U.S. Pat. Nos. 4,693,935, 4,728,571, and 4,972,037. These polymers may, for example, be anionic or nonionic.

Such polymers are, for example, copolymers that can be obtained by free-radical polymerization starting with a monomer mixture comprising:

a) 50 to 90% by weight of tert-butyl acrylate;
b) 0 to 40% by weight of acrylic acid; and
c) 5 to 40% by weight of silicone macromer of formula:

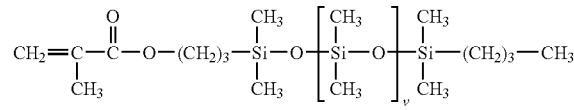

wherein v is a number ranging from 5 to 700; the weight percentages being calculated relative to the total weight of the monomers.

Other examples of grafted silicone polymers include polydimethylsiloxanes (PDMS) onto which are grafted, via a connecting chain unit of thiopropylene, mixed polymer units of poly(meth)acrylic acid and polyalkyl(meth)acrylate and polydimethylsiloxanes (PDMS) onto which are grafted, via a connecting chain unit of thiopropylene, polymer units of polyisobutyl(meth)acrylate.

In one embodiment, all of the silicones can also be used in the form of emulsions.

In one embodiment, the polyorganosiloxanes that may be used in the composition disclosed herein may be non-volatile silicones chosen from polyalkylsiloxanes comprising trimethylsilyl end groups, such as polydimethylsiloxane oils having a viscosity ranging from 0.2 to 2.5 m²/s at 25° C. of the Silbione 70047 and 47 series and, further, for example, the oil 70 047 V 500 000, which are sold by the company Rhodia Chimie, polyalkylsiloxanes comprising dimethylsilanol end groups, and polyalkylarylsiloxanes, such as the oil Silbione 70641 V 200 sold by the company Rhodia Chimie;

The at least one non-amino, non-volatile silicone may be present in an amount ranging from 0.05% to 10% by weight, further, for example, from 0.1% to 5% by weight, and even further, for example, from 0.2% to 3% by weight, relative to the total weight of the composition.

The medium that is suitable for the cosmetic composition disclosed herein may comprise water and mixtures of water and at least one organic solvent to dissolve the compounds that would not be sufficiently water-soluble. Examples of the at least one organic solvent that may used include $C_1$-$C_4$ lower alkanols, such as ethanol and isopropanol; polyols and polyol ethers, for example, 2-butoxyethanol, propylene glycol, propylene glycol monomethyl ether, diethylene glycol monoethyl ether and monomethyl ether, and also aromatic alcohols, example, benzyl alcohol and phenoxyethanol.

The at least one organic solvent may be present in an amount ranging from 1% to 40% by weight and, further, for example, from 5% to 30% by weight, relative to the total weight of the composition.

The cosmetic composition disclosed herein may also comprise at least one adjuvant conventionally used in cosmetic compositions, chosen from cationic and nonionic surfactants; cationic polymers other than those disclosed herein; anionic, nonionic, amphoteric, and zwitterionic polymers; mineral and organic thickeners, for example, anionic, cationic, nonionic and amphoteric polymeric associative thickeners; antioxidants; penetrating agents; sequestering agents; fragrances; buffers; dispersants; conditioners other than those disclosed herein; film-forming agents; ceramides; preserving agents; opacifiers; and nacreous agents.

The at least one adjuvant may be present in an amount ranging from 0.01% to 20% by weight, relative to the total weight of the composition.

A person skilled in the art will take care to select this or these complementary compound(s) such that the advantageous properties intrinsically associated with the cosmetic composition in accordance with this disclosure are not, or are not substantially, adversely affected by the envisaged addition(s).

The pH of the cosmetic composition disclosed herein ranges from 2 to 12, further, for example, from 3 to 11 and, further, for example, from 5 to 8.

Also disclosed herein is a cosmetic treatment process comprising applying at least one composition to keratin fibers, rinsing the fibers, after an optional leave-in time ranging from 15 seconds to 15 minutes.

The examples that follow illustrate the present disclosure without limiting its scope.

EXAMPLE 1

The inventor prepared a composition according to the present disclosure and a composition of the prior art. Their formulation is defined in the following table:

| Composition | Invention | Comparative |
|---|---|---|
| Sodium lauryl ether sulfate containing 2.2 mol of ethylene oxide | 15 g AM | 15 g AM |
| Cocoamidopropylbetaine | 2.4 g AM | 2.4 g AM |
| Dimethyldiallylammonium chloride/acrylamide copolymer (50/50) as an aqueous solution containing 8.7% A.M., sold under the name Merquat S by the company Nalco | 1.5 g (0.13 g AM) | 1.5 g (0.13 g AM) |
| Guar gum modified with 2,3-epoxypropyl-trimethylammonium chloride, sold under the name Jaguar C13 S by the company Rhodia | 0.1 g | 0.1 g |
| Polydimethylsiloxane sold under the name DC 200 Fluid 350 cS by the company Dow Corning (non-volatile silicone) | 2.7 g | — |
| Cyclopentadimethylsiloxane/cyclohexadimethylsiloxane mixture sold under the name DC 345 Fluid by the company Dow Corning (volatile silicone) | — | 2.7 g |
| Distearyl ether | 1.5 g | 1.5 g |
| Behenyl alcohol | 1.5 g | 1.5 g |
| Crosslinked polyacrylic acid | 0.2 g | 0.2 g |
| Coconut acid monoisopropanolamide | 1.0 g | 1.0 g |
| Preserving agents, fragrance | qs | qs |
| pH agent qs | pH 7 | pH 7 |
| Demineralized water qs | 100 g | 100 g |

Comparative tests between these two compositions were performed on ten models with sensitized hair. The tests demonstrated that the composition according to the present disclosure made it possible to obtain:

a more abundant lather in 70% of cases, a less coarse feel of the wet hair in 80% of cases.

Furthermore, the formulation according to the present disclosure was stable after two months of storage at 45° C., unlike the comparative composition.

EXAMPLE 2

The inventor prepared the following composition according to the present disclosure:

| | |
|---|---|
| Sodium lauryl ether sulfate containing 2.2 mol of ethylene oxide | 15 g AM |
| Cocoamidopropylbetaine | 2.4 g AM |
| Dimethyldiallylammonium chloride/acrylamide copolymer (50/50) as an aqueous solution containing 8.7%, sold under the name Merquat S by the company Nalco | 1.5 g |
| Guar gum modified with 2,3-epoxypropyltrimethyl-ammonium chloride, sold under the name Jaguar C13 S by the company Rhodia | 0.1 g |
| Polydimethylsiloxane sold under the name DC 200 Fluid 300 000 by the company Dow Corning | 2.7 g |
| Distearyl ether | 1.5 g |
| Behenyl alcohol | 1.5 g |
| Crosslinked polyacrylic acid | 0.2 g |

| | |
|---|---|
| Coconut acid monoisopropanolamide | 1.0 g |
| Preserving agents, fragrance | qs |
| pH agent qs | pH 7 |
| Demineralized water qs | 100 g |

This composition made curly hair smooth and led to good curl definition. The curls were tonic and smooth.

What is claimed is:

1. A cosmetic composition for treating keratin fibers comprising:
   from 0.5% to 19% by weight of at least one anionic surfactant, relative to the total weight of the composition;
   from 0.5% to 10% by weight of at least one second surfactant, relative to the total weight of the composition, wherein the at least one second surfactant is chosen from amphoteric and zwitterionic surfactants chosen from $(C_8\text{-}C_{20})$alkylbetaines, sulfobetaines, $(C_8\text{-}C_{20})$alkylamido$(C_1\text{-}C_6)$alkylbetaines, $(C_8\text{-}C_{20})$alkylamido$(C_1\text{-}C_6)$alkylsulfobetaines, and amines of formulae (I) and (II):

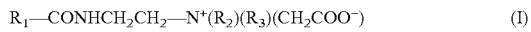
$$R_1\text{—CONHCH}_2\text{CH}_2\text{—N}^+(R_2)(R_3)(CH_2COO^-) \quad (I)$$

wherein:
   $R_1$ is chosen from $C_5\text{-}C_{20}$ linear and branched alkyl radicals derived from an acid $R_1$—COOH present in hydrolyzed coconut oil
   $R_2$ is a beta-hydroxyethyl group; and
   $R_3$ is chosen from a carboxymethyl group; and

$$R_4\text{—CONH CH}_2\text{CH}_2\text{—N(B)(D)} \quad (II)$$

wherein:
   B is chosen from groups —CH$_2$CH$_2$OX;
   D is chosen from groups —(CH$_2$)$_z$—Y, wherein z=1 or 2;
   X is chosen from a —CH$_2$CH$_2$—COOH group and a hydrogen atom;
   Y is chosen from —COOH and —CH$_2$—CHOH—SO$_3$H radicals; and
   $R_4$ is chosen from $C_5\text{-}C_{20}$, saturated or unsaturated, linear or branched alkyl radicals derived from an acid $R_4$—COOH
   from 0.01% to 10% by weight of at least one first cationic polymer, relative to the total weight of the composition, wherein the at least one first cationic polymer is chosen from cationic guar gums;
   from 0.01% to 10% by weight of at least one second cationic polymer, relative to the total weight of the composition, wherein the at least one second cationic polymer is chosen from dialkyldiallylammonium homopolymers and dialkyldiallylammonium copolymers; and
   from 0.05% to 10% by weight of at least one non-amino non-volatile silicone, relative to the total weight of the composition, wherein the at least one non-amino non-volatile silicone is chosen from polyalkylsiloxanes;
wherein the total amount of surfactants in the composition ranges from 4.5% to 20% by weight, relative to the total weight of the composition.

2. The composition according to claim 1, wherein the keratin fibers are hair.

3. The composition according to claim 1, wherein the at least one anionic surfactant is chosen from alkali metal salts, ammonium salts, amine salts, amino alcohol salts and magnesium salts, of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; $(C_6\text{-}C_{24})$alkyl sulfosuccinates, $(C_6\text{-}C_{24})$alkyl ether sulfosuccinates, $(C_6\text{-}C_{24})$alkylamide sulfosuccinates; $(C_6\text{-}C_{24})$alkyl sulfoacetates; $(C_6\text{-}C_{24})$acyl sarcosinates; and $(C_6\text{-}C_{24})$acyl glutamates; $(C_6\text{-}C_{24})$alkylpolyglycoside carboxylic esters, acyl isethionates, N-acyl taurates; fatty acid salts and acyl lactylates; alkyl D-galactoside uronic acids, polyoxyalkylenated $(C_6\text{-}C_{24})$alkyl ether carboxylic acids, polyoxyalkylenated $(C_6\text{-}C_{24})$alkylaryl ether carboxylic acids and polyoxyalkylenated $(C_6\text{-}C_{24})$alkylamido ether carboxylic acids, and salts thereof.

4. The composition according to claim 1, wherein the cationic guar gums comprise at least one trialkylammonium cationic group.

5. The composition according to claim 1, wherein the cationic guar gums are modified with at least one salt chosen from 2,3-epoxypropyltrimethylammonium, glycidyltrimethylammonium, and 3-chloro-2-hydroxypropyltrimethylammonium salts.

6. The composition according to claim 1, wherein the at least one second cationic polymer is chosen from dialkyldiallylammonium homopolymers and copolymers comprising, as a main constituent of the chain, at least one unit chosen from units corresponding to formula (III) and (IV) below:

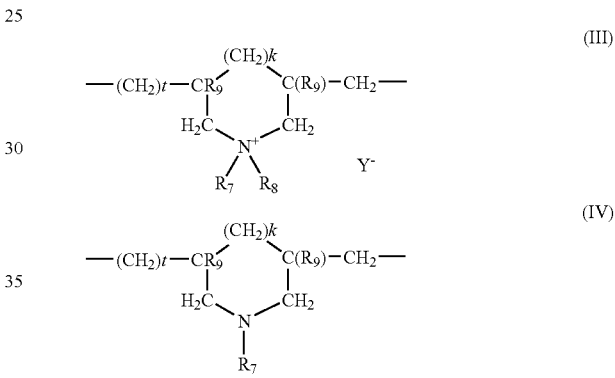

wherein:
   k and t are equal to 0 or 1, wherein the sum k+t is equal to 1;
   $R_9$ is chosen from a hydrogen atom and methyl radicals;
   $R_7$ and $R_8$, which may be identical or different, are each chosen from alkyl groups comprising from 1 to 6 carbon atoms, hydroxyalkyl groups, lower $(C_1\text{-}C_4)$ amidoalkyl groups, or $R_7$ and $R_7$ form, together with the nitrogen atom to which they are attached, at least one heterocyclic group; and
   $Y^-$ is an anion.

7. The composition according to claim 6, wherein the alkyl groups, of the hydroxyalkyl groups of $R_7$ and $R_8$, are chosen from alkyl groups comprising from 1 to 5 carbon atoms.

8. The composition according to claim 6, wherein the at least one heterocyclic group, formed by $R_7$ and $R_8$ and the nitrogen atom to which they are attached, is chosen from piperidyl and morpholinyl groups.

9. The composition according to claim 6, wherein $R_7$ and $R_8$, which may be identical or different, are each chosen from alkyl groups comprising from 1 to 4 carbon atoms.

10. The composition according to claim 6, wherein $Y^-$ is an anion chosen from bromide, chloride, acetate, borate, citrate, tartrate, bisulfate, bisulfite, sulfate, and phosphate.

11. The composition according to claim 1, wherein the at least one second cationic polymer is chosen from diallyldimethylammonium homopolymers and copolymers.

12. The composition according to claim 1, wherein the polyalkylsiloxanes comprise trimethylsilyl end groups.

13. The composition according to claim 1, wherein the at least one anionic surfactant and the at least one second surfactant are present such that the weight ratio of the at least one anionic surfactant to the at least one second surfactant is greater than 1.5:1.

14. The composition according to claim 1, wherein the at least one anionic surfactant and the at least one second surfactant are present such that the weight ratio of the at least one anionic surfactant to the at least one second surfactant ranges from 2:1 to 20:1.

15. The composition according to claim 1, wherein the at least one first cationic polymer is present in an amount ranging from 0.03% to 5% by weight, relative to the total weight of the composition.

16. The composition according to claim 1, wherein the at least one second cationic polymer is present in an amount ranging from 0.03% to 5% by weight, relative to the total weight of the composition.

17. The composition according to claim 1, wherein the at least one non-amino non-volatile silicone is present in an amount ranging from 0.1% to 5% by weight, relative to the total weight of the composition.

18. The composition according to claim 1, wherein the composition has a pH ranging from 2 to 12.

19. The composition according to claim 1, comprising at least one adjuvant chosen from cationic and nonionic surfactants; cationic polymers other than the at least first cationic polymer and the at least one second cationic polymer; anionic, nonionic, amphoteric, and zwitterionic polymers; mineral and organic thickeners; antioxidants; penetrating agents; sequestering agents; fragrances; buffers; dispersants; conditioners other than the at least first cationic polymer and the at least one second cationic polymer; film-forming agents; ceramides; preserving agents; and opacifiers.

20. A cosmetic process for treating keratin fibers comprising:
applying to the fibers at least one cosmetic composition comprising,
(a) from 0.5% to 19% by weight of at least one anionic surfactant, relative to the total weight of the composition;
(b) from 0.5% to 10% by weight of at least one second surfactant, relative to the total weight of the composition, wherein the at least one second surfactant is chosen from amphoteric and zwitterionic surfactants chosen from $(C_8-C_{20})$alkylbetaines, sulfobetaines, $(C_8-C_{20})$alkylamido$(C_1-C_6)$alkylbetaines, $(C_8-C_{20})$alkylamido$(C_1-C_6)$alkylsulfobetaines, and amines of formulae (I) and (II):

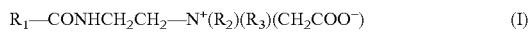

wherein:
$R_1$ is chosen from $C_5-C_{20}$ linear and branched alkyl radicals derived from an acid $R_1$—COOH resent in hydrolyzed coconut oil
$R_2$ is a beta-hydroxyethyl group; and
$R_3$ is chosen from a carboxymethyl group; and

wherein:
B is chosen from groups —CH$_2$CH$_2$OX;
D is chosen from groups —(CH$_2$)$_z$—Y, wherein z=1 or 2;
X is chosen from a —CH$_2$CH$_2$—COOH group and a hydrogen atom;
Y is chosen from —COOH and —CH$_2$—CHOH—SO$_3$H radicals; and
$R_4$ is chosen from $C_5-C_{20}$, saturated or unsaturated, linear or branched alkyl radicals derived from an acid $R_4$—COOH
(c) from 0.01% to 10% by weight of at least one first cationic polymer, relative to the total weight of the composition, wherein the at least one second cationic polymer is chosen from cationic guar gums;
(d) from 0.01% to 10% by weight of at least one second cationic polymer, relative to the total weight of the composition, wherein the at least one second cationic polymer is chosen from dialkyldiallylammonium homopolymers and dialkyldiallylammonium copolymers; and
(e) from 0.05% to 10% by weight of at least one non-amino non-volatile silicone, relative to the total weight of the composition, wherein the at least one non-amino non-volatile silicone is chosen from polyalkylsiloxanes,
wherein the total amount of surfactants in the composition ranges from 4.5% to 20% by weight, relative to the total weight of the composition;
leaving the at least one cosmetic composition on the fibers for a time period ranging from 15 seconds to 15 minutes; and
rinsing of the fibers.

21. A method for improving at least one quality of curly hair comprising applying, to the hair, at least one cosmetic composition comprising,
from 0.5% to 19% by weight of at least one anionic surfactant, relative to the total weight of the composition;
from 0.5% to 10% by weight of at least one second surfactant, relative to the total weight of the composition, wherein the at least one second surfactant is chosen from amphoteric and zwitterionic surfactants chosen from $(C_8-C_{20})$alkylbetaines, sulfobetaines, $(C_8-C_{20})$alkylamido$(C_1-C_6)$alkylbetaines, $(C_8-C_{20})$alkylamido$(C_1-C_6)$alkylsulfobetaines, and amines of formulae (I) and (II):

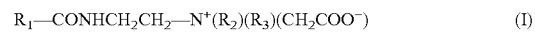

wherein:
$R_1$ is chosen from $C_5-C_{20}$ linear and branched alkyl radicals derived from an acid $R_1$—COOH present in hydrolyzed coconut oil
$R_2$ is a beta-hydroxyethyl group; and
$R_3$ is chosen from a carboxymethyl group; and

wherein:
B is chosen from groups —CH$_2$CH$_2$OX;
D is chosen from groups —(CH$_2$)$_z$—Y, wherein z=1 or 2;
X is chosen from a —CH$_2$CH$_2$—COOH group and a hydrogen atom;
Y is chosen from —COOH and —CH$_2$—CHOH—SO$_3$H radicals; and
$R_4$ is chosen from $C_5-C_{20}$, saturated or unsaturated, linear or branched alkyl radicals derived from an acid $R_4$—COOH
from 0.01% to 10% by weight of at least one first cationic polymer, relative to the total weight of the composition, wherein the at least one first cationic polymer is chosen from cationic guar gums;
from 0.01% to 10% by weight of at least one second cationic polymer, relative to the total weight of the composition, wherein the at least one second cationic polymer is chosen from dialkyldiallylammonium homopolymers and dialkyldiallylammonium copolymers; and from 0.05% to 10% by weight of at least one non-amino non-volatile silicone, relative to the total weight of the composition, wherein the at least one non-amino non-volatile silicone is chosen from polyalkylsiloxanes; wherein the total amount of surfactants in the composition ranges from 4.5% to 20% by weight, relative to the total weight of the composition.

22. The method according to claim 21, wherein the at least one quality is tonicity.

* * * * *

UNITED STATES PATENT AND TRADEMARK OFFICE
CERTIFICATE OF CORRECTION

PATENT NO. : 7,811,552 B2  
APPLICATION NO. : 10/900086  
DATED : October 12, 2010  
INVENTOR(S) : Mireille Maubru et al.

Page 1 of 1

It is certified that error appears in the above-identified patent and that said Letters Patent is hereby corrected as shown below:

In The Claims

Claim 1, col. 11, line 28, "coconut oil" should read --coconut oil;--.

Claim 1, col. 11, line 42, "$R_4$—COOH" should read --$R_4$—COOH;--.

Claim 20, col. 13, line 58, "coconut oil" should read --coconut oil;--.

Claim 20, col. 14, line 5, "$R_4$—COOH" should read --$R_4$—COOH;--.

Claim 21, col. 14, line 46, "coconut oil" should read --coconut oil;--.

Claim 21, col. 14, line 59, "$R_4$—COOH" should read --$R_4$—COOH;--.

Signed and Sealed this  
Twenty-second Day of February, 2011

David J. Kappos  
*Director of the United States Patent and Trademark Office*